(12) United States Patent
Dunki-Jacobs

(10) Patent No.: US 7,995,045 B2
(45) Date of Patent: Aug. 9, 2011

(54) COMBINED SBI AND CONVENTIONAL IMAGE PROCESSOR

(75) Inventor: Robert J. Dunki-Jacobs, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1152 days.

(21) Appl. No.: 11/786,858

(22) Filed: Apr. 13, 2007

(65) Prior Publication Data

US 2008/0252778 A1   Oct. 16, 2008

(51) Int. Cl.
*G06F 3/038* (2006.01)
(52) U.S. Cl. .................. 345/204; 348/441; 359/224
(58) Field of Classification Search .............. 345/204; 348/E3.009, E5.078, E5.09, E7.084, 205; 348/441; 359/224
See application file for complete search history.

(56) References Cited

U.S. PATENT DOCUMENTS

| 3,758,199 A | 9/1973 | Thaxter |
|---|---|---|
| 3,959,582 A | 5/1976 | Law et al. |
| 4,082,635 A | 4/1978 | Fritz et al. |
| 4,141,362 A | 2/1979 | Wurster |
| 4,313,431 A | 2/1982 | Frank |
| 4,379,039 A | 4/1983 | Fujimoto et al. |
| 4,403,273 A | 9/1983 | Nishioka |
| 4,409,477 A | 10/1983 | Carl |
| 4,421,382 A | 12/1983 | Doi et al. |
| 4,524,761 A | 6/1985 | Hattori et al. |
| 4,527,552 A | 7/1985 | Hattori |
| 4,573,465 A | 3/1986 | Sugiyama et al. |
| 4,576,999 A | 3/1986 | Eckberg |
| 4,597,380 A | 7/1986 | Raif et al. |
| 4,643,967 A | 2/1987 | Bryant |
| 4,676,231 A | 6/1987 | Hisazumi et al. |
| 4,760,840 A | 8/1988 | Fournier, Jr. et al. |
| 4,803,550 A | 2/1989 | Yabe et al. |
| 4,872,458 A | 10/1989 | Kanehira et al. |
| 4,902,083 A | 2/1990 | Wells |

(Continued)

FOREIGN PATENT DOCUMENTS

DE  3837248  5/1990

(Continued)

OTHER PUBLICATIONS

Kiang, M-H et al., "Surface-Micromachined Electrostatic-Comb Driven Scanning Micromirrors for Barcode Scanners" (date of first publication unknown).

(Continued)

*Primary Examiner* — Kimnhung Nguyen
(74) *Attorney, Agent, or Firm* — Victor C. Moreno

(57) ABSTRACT

An apparatus and method for allowing multiple high and low resolution SBI and conventional FPA imaging devices to use a common high resolution monitor and archive device without increasing or significantly changing the footprint of existing devices. This system and method uses a frame grabber for digitizing video from the legacy FPA devices, a frame mapper for rendering or mapping the FPA video into the SBI digital format, a converter for rasterizing SBI data streams into pixel-oriented FPA video frames, an input selector for selecting which FPA or SBI imaging device to display on a high resolution monitor, an processor for storing and manipulating frames of video, a video output encoder for converting the SBI frames into a video signal appropriate for display on the high resolution monitor, and an output means for connecting to a storage device for archiving video and images.

26 Claims, 5 Drawing Sheets

U.S. PATENT DOCUMENTS

| | | |
|---|---|---|
| 4,902,115 A | 2/1990 | Takahashi |
| 4,934,773 A | 6/1990 | Becker |
| 4,938,205 A | 7/1990 | Nudelman |
| 5,003,300 A | 3/1991 | Wells |
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A | 5/1993 | Sinofsky |
| 5,218,195 A | 6/1993 | Hakamata |
| 5,251,025 A | 10/1993 | Cooper et al. |
| 5,251,613 A | 10/1993 | Adair |
| 5,269,289 A | 12/1993 | Takehana et al. |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,436,655 A | 7/1995 | Hiyama et al. |
| 5,467,104 A | 11/1995 | Furness, III et al. |
| 5,488,862 A | 2/1996 | Neukermans et al. |
| 5,531,740 A | 7/1996 | Black |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A | 3/1997 | Konno et al. |
| 5,629,790 A | 5/1997 | Neukermans et al. |
| 5,648,618 A | 7/1997 | Neukermans et al. |
| 5,649,952 A | 7/1997 | Lam |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A | 5/2000 | Furusawa et al. |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 | 4/2001 | Lai |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,366,319 B1 * | 4/2002 | Bills ............................ 348/273 |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |

| | | | | | | |
|---|---|---|---|---|---|---|
| 6,445,362 B1 | 9/2002 | Tegreene | | 6,978,921 B2 | 12/2005 | Shelton, IV et al. |
| 6,447,524 B1 | 9/2002 | Knodel et al. | | 6,985,271 B2 | 1/2006 | Yazdi et al. |
| 6,462,770 B1 | 10/2002 | Cline et al. | | 6,991,602 B2 | 1/2006 | Nakazawa et al. |
| 6,464,363 B1 | 10/2002 | Nishioka et al. | | 7,005,195 B2 | 2/2006 | Cheng et al. |
| 6,467,345 B1 | 10/2002 | Neukermans et al. | | 7,009,634 B2 | 3/2006 | Iddan et al. |
| 6,470,124 B1 | 10/2002 | Le Gargasson et al. | | 7,013,730 B2 | 3/2006 | Malametz |
| 6,477,403 B1 | 11/2002 | Eguchi et al. | | 7,015,956 B2 | 3/2006 | Luo et al. |
| 6,478,809 B1 | 11/2002 | Brotz | | 7,018,401 B1 | 3/2006 | Hyodoh et al. |
| 6,485,413 B1 | 11/2002 | Boppart et al. | | 7,023,402 B2 | 4/2006 | Lewis et al. |
| 6,492,962 B2 | 12/2002 | Melville et al. | | 7,025,777 B2 | 4/2006 | Moore |
| 6,494,578 B1 | 12/2002 | Plummer et al. | | 7,033,348 B2 | 4/2006 | Alfano et al. |
| 6,503,196 B1 | 1/2003 | Kehr et al. | | 7,035,475 B1* | 4/2006 | Chen et al. ................. 382/254 |
| 6,510,338 B1 | 1/2003 | Irion et al. | | 7,035,777 B2 | 4/2006 | Araki et al. |
| 6,512,622 B2 | 1/2003 | Wine et al. | | 7,061,450 B2 | 6/2006 | Bright et al. |
| 6,513,939 B1 | 2/2003 | Fettig et al. | | 7,065,301 B2 | 6/2006 | Shastri et al. |
| 6,515,278 B2 | 2/2003 | Wine et al. | | 7,066,879 B2 | 6/2006 | Fowler et al. |
| 6,515,781 B2 | 2/2003 | Lewis et al. | | 7,071,594 B1 | 7/2006 | Yan et al. |
| 6,520,972 B2 | 2/2003 | Peters | | 7,071,931 B2 | 7/2006 | Tegreene et al. |
| 6,522,444 B2 | 2/2003 | Mandella et al. | | 7,078,378 B1 | 7/2006 | Owen et al. |
| 6,525,310 B2 | 2/2003 | Dunfield | | 7,108,656 B2 | 9/2006 | Fujikawa et al. |
| 6,527,708 B2 | 3/2003 | Nakamura et al. | | 7,112,302 B2 | 9/2006 | Yoshimi et al. |
| 6,529,770 B1 | 3/2003 | Grimblatov | | 7,126,903 B2 | 10/2006 | Feenstra et al. |
| 6,530,698 B1 | 3/2003 | Kuhara et al. | | 7,189,961 B2 | 3/2007 | Johnston et al. |
| 6,535,183 B2 | 3/2003 | Melville et al. | | 7,190,329 B2 | 3/2007 | Lewis et al. |
| 6,535,325 B2 | 3/2003 | Helsel et al. | | 7,232,071 B2 | 6/2007 | Lewis et al. |
| 6,537,211 B1 | 3/2003 | Wang et al. | | 7,271,383 B2 | 9/2007 | Chee |
| 6,538,625 B2 | 3/2003 | Tidwell et al. | | 7,391,013 B2 | 6/2008 | Johnston et al. |
| 6,545,260 B1 | 4/2003 | Katashiro et al. | | 2001/0055462 A1 | 12/2001 | Seibel |
| 6,560,028 B2 | 5/2003 | Melville et al. | | 2002/0015724 A1 | 2/2002 | Yang et al. |
| 6,563,105 B2 | 5/2003 | Seibel et al. | | 2002/0024495 A1 | 2/2002 | Lippert et al. |
| 6,563,106 B1 | 5/2003 | Bowers et al. | | 2002/0050956 A1 | 5/2002 | Gerhard et al. |
| 6,572,606 B2 | 6/2003 | Kliewer et al. | | 2002/0075284 A1 | 6/2002 | Rabb, III |
| 6,583,117 B2 | 6/2003 | Owen et al. | | 2002/0088925 A1 | 7/2002 | Nestorovic et al. |
| 6,583,772 B1 | 6/2003 | Lewis et al. | | 2002/0115922 A1 | 8/2002 | Waner et al. |
| 6,585,642 B2 | 7/2003 | Christopher | | 2002/0141026 A1 | 10/2002 | Wiklof et al. |
| 6,603,552 B1 | 8/2003 | Cline et al. | | 2002/0158814 A1 | 10/2002 | Bright et al. |
| 6,608,297 B2 | 8/2003 | Neukermans et al. | | 2002/0163484 A1 | 11/2002 | Furness, III et al. |
| 6,639,570 B2 | 10/2003 | Furness, III et al. | | 2002/0167462 A1 | 11/2002 | Lewis et al. |
| 6,639,719 B2 | 10/2003 | Tegreene et al. | | 2002/0171776 A1 | 11/2002 | Tegreene et al. |
| 6,650,877 B1 | 11/2003 | Tarbouriech et al. | | 2002/0171937 A1 | 11/2002 | Tegreene et al. |
| 6,653,621 B2 | 11/2003 | Wine et al. | | 2003/0016187 A1 | 1/2003 | Melville et al. |
| 6,654,158 B2 | 11/2003 | Helsel et al. | | 2003/0030753 A1 | 2/2003 | Kondo et al. |
| 6,661,393 B2 | 12/2003 | Tegreene et al. | | 2003/0032143 A1 | 2/2003 | Neff et al. |
| 6,674,993 B1 | 1/2004 | Tarbouriech | | 2003/0034709 A1 | 2/2003 | Jerman |
| 6,685,804 B1 | 2/2004 | Ikeda et al. | | 2003/0058190 A1 | 3/2003 | Lewis et al. |
| 6,687,034 B2 | 2/2004 | Wine et al. | | 2003/0086172 A1 | 5/2003 | Urey |
| 6,689,056 B1 | 2/2004 | Kilcoyne et al. | | 2003/0092995 A1 | 5/2003 | Thompson |
| 6,699,170 B1 | 3/2004 | Crocker et al. | | 2003/0130562 A1 | 7/2003 | Barbato et al. |
| 6,700,552 B2 | 3/2004 | Kollin et al. | | 2003/0142934 A1 | 7/2003 | Pan et al. |
| 6,714,331 B2 | 3/2004 | Lewis et al. | | 2003/0159447 A1 | 8/2003 | Sergio et al. |
| 6,734,835 B2 | 5/2004 | Tidwell et al. | | 2003/0214460 A1 | 11/2003 | Kovacs |
| 6,736,511 B2 | 5/2004 | Plummer et al. | | 2003/0216729 A1 | 11/2003 | Marchitto et al. |
| 6,741,884 B1 | 5/2004 | Freeman et al. | | 2003/0222860 A1* | 12/2003 | Yamaura ...................... 345/204 |
| 6,749,346 B1 | 6/2004 | Dickensheets et al. | | 2004/0004585 A1 | 1/2004 | Brown et al. |
| 6,755,536 B2 | 6/2004 | Tegreene et al. | | 2004/0057103 A1 | 3/2004 | Bernstein |
| 6,762,867 B2 | 7/2004 | Lippert et al. | | 2004/0075624 A1 | 4/2004 | Tegreene et al. |
| 6,768,588 B2 | 7/2004 | Urey | | 2004/0076390 A1 | 4/2004 | Dong Yang et al. |
| 6,771,001 B2 | 8/2004 | Mao et al. | | 2004/0085261 A1 | 5/2004 | Lewis et al. |
| 6,782,748 B2 | 8/2004 | Weber et al. | | 2004/0085617 A1 | 5/2004 | Helsel et al. |
| 6,786,382 B1 | 9/2004 | Hoffman | | 2004/0087844 A1 | 5/2004 | Yen |
| 6,795,221 B1 | 9/2004 | Urey | | 2004/0101822 A1 | 5/2004 | Wiesner et al. |
| 6,802,809 B2 | 10/2004 | Okada | | 2004/0113059 A1 | 6/2004 | Kawano et al. |
| 6,803,561 B2 | 10/2004 | Dunfield | | 2004/0118821 A1 | 6/2004 | Han et al. |
| 6,821,245 B2 | 11/2004 | Cline et al. | | 2004/0119004 A1 | 6/2004 | Wine et al. |
| 6,845,190 B1 | 1/2005 | Smithwick et al. | | 2004/0122328 A1 | 6/2004 | Wang et al. |
| 6,856,436 B2 | 2/2005 | Brukilacchio et al. | | 2004/0133786 A1 | 7/2004 | Tarbouriech |
| 6,856,712 B2 | 2/2005 | Fauver et al. | | 2004/0151466 A1 | 8/2004 | Crossman-Bosworth et al. |
| 6,879,428 B2 | 4/2005 | Massieu | | 2004/0155186 A1 | 8/2004 | Nestorovic et al. |
| 6,888,552 B2 | 5/2005 | Debevec et al. | | 2004/0155834 A1 | 8/2004 | Wit et al. |
| 6,894,823 B2 | 5/2005 | Taylor et al. | | 2004/0179254 A1 | 9/2004 | Lewis et al. |
| 6,899,675 B2 | 5/2005 | Cline et al. | | 2004/0196518 A1 | 10/2004 | Wine et al. |
| 6,902,527 B1 | 6/2005 | Doguchi et al. | | 2004/0223202 A1 | 11/2004 | Lippert et al. |
| 6,905,057 B2 | 6/2005 | Swayze et al. | | 2004/0225222 A1 | 11/2004 | Zeng et al. |
| 6,939,364 B1 | 9/2005 | Soltz et al. | | 2004/0236371 A1 | 11/2004 | McNally-Heintzelman et al. |
| 6,957,898 B2 | 10/2005 | Yu | | 2004/0240866 A1 | 12/2004 | Ramsbottom |
| 6,967,757 B1 | 11/2005 | Allen et al. | | 2004/0252377 A1 | 12/2004 | Urey |
| 6,974,472 B2 | 12/2005 | Hong et al. | | 2004/0254474 A1 | 12/2004 | Seibel et al. |
| 6,975,898 B2 | 12/2005 | Seibel | | 2005/0010787 A1 | 1/2005 | Tarbouriech |
| 6,976,994 B2 | 12/2005 | Ballou et al. | | 2005/0014995 A1 | 1/2005 | Amundson et al. |

| | | | |
|---|---|---|---|
| 2005/0020877 A1 | 1/2005 | Ishihara et al. | |
| 2005/0020926 A1* | 1/2005 | Wiklof et al. | 600/476 |
| 2005/0023356 A1 | 2/2005 | Wiklof et al. | |
| 2005/0030305 A1 | 2/2005 | Brown et al. | |
| 2005/0038322 A1 | 2/2005 | Banik | |
| 2005/0116038 A1 | 6/2005 | Lewis et al. | |
| 2005/0162762 A1 | 7/2005 | Novak | |
| 2005/0187441 A1 | 8/2005 | Kawasaki et al. | |
| 2005/0203343 A1 | 9/2005 | Kang et al. | |
| 2005/0240147 A1 | 10/2005 | Makower et al. | |
| 2006/0010985 A1 | 1/2006 | Schneider | |
| 2006/0084867 A1 | 4/2006 | Tremblay et al. | |
| 2006/0164330 A1 | 7/2006 | Bright et al. | |
| 2006/0183246 A1 | 8/2006 | Wiesner et al. | |
| 2006/0195014 A1 | 8/2006 | Seibel et al. | |
| 2006/0238774 A1 | 10/2006 | Lindner et al. | |
| 2006/0245971 A1 | 11/2006 | Burns et al. | |
| 2006/0284790 A1 | 12/2006 | Tegreene et al. | |
| 2007/0038119 A1 | 2/2007 | Chen et al. | |
| 2007/0046778 A1 | 3/2007 | Ishihara et al. | |
| 2007/0135770 A1 | 6/2007 | Hunt et al. | |
| 2007/0156021 A1 | 7/2007 | Morse et al. | |
| 2007/0161876 A1 | 7/2007 | Bambot et al. | |
| 2007/0162093 A1 | 7/2007 | Porter et al. | |
| 2007/0167681 A1 | 7/2007 | Gill et al. | |
| 2007/0173707 A1 | 7/2007 | Mitra | |
| 2007/0179366 A1 | 8/2007 | Pewzner et al. | |
| 2007/0197874 A1 | 8/2007 | Ishihara | |
| 2007/0197875 A1 | 8/2007 | Osaka | |
| 2007/0203413 A1 | 8/2007 | Frangioni | |
| 2007/0213588 A1 | 9/2007 | Morishita et al. | |
| 2007/0213618 A1 | 9/2007 | Li et al. | |
| 2007/0225695 A1 | 9/2007 | Mayer et al. | |
| 2007/0238930 A1 | 10/2007 | Wiklof et al. | |
| 2007/0244365 A1 | 10/2007 | Wiklof | |
| 2007/0260121 A1 | 11/2007 | Bakos et al. | |
| 2007/0260273 A1 | 11/2007 | Cropper et al. | |
| 2007/0272841 A1* | 11/2007 | Wiklof | 250/234 |
| 2008/0058629 A1 | 3/2008 | Seibel et al. | |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Lewis, J.R. et al., "Scanned beam medical imager," MOEMS Display and Imaging Systems II, Proceedings of SPIE vol. 5348, pp. 40-51 (2004).

James, R. et al., "Update on MEMS-based Scanned Beam Imager" (date of first publication unknown).

Wiklof, C., "Display technology spawns laser camera," Laser Focus World (Dec. 2004).

"Press Information—Phillips' Fluid Lenses Bring Things into Focus," http://www.newscenter.philips.com (Mar. 3, 2004).

Lettice, J., "The $5 'no moving parts' fluid zoom lens—twice," The Register (Mar. 15, 2004).

"Volcano Products—IVUS Imaging Visions® PV018," http://www.volcanotherapeutics.com (date of first publication unknown).

Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).

"Crystalplex Technology—PlxBead™ Superior Qualities," http:www.crystalplex.com (date of first publication unknown).

"Microvision [illuminating information] Products/Overview, Corporate Overview Presentation 2006" (2006).

"Holographic Beam Combiner for Ladar, Printer, Fiber Optics, and Cancer Treatment," by Digital Optics Technologies, Inc., http://www.mdatechnology.net (date of first publication unknown).

Brown, D.M., Abstract from SPIE Digital Library for "High-power laser diode beam combiner," Optical Engineering, vol. 42, Issue 11 (2003).

Literature entitled "All fiber beam combiner from Point Source" (Oct. 13, 2006).

"Custom Polarzing Cube Beamsplitters," from GlobalSpec The Engineering Search Engine, http://www.globalspec.com (date of first publication unknown).

Literature entitled "Dallas Semiconductor MAXIM—Visible-Laser Driver has Digitally Controlled Power Modulation," by Maxim Integrated Products, http://www.maxim-ic.com (Jul. 1, 2001).

"SCAN Mode Strategies for SCUBA-2" (May 25, 2005).

Seifert, M. et al., "High Power Diode Laser Beam Scanning in Multi-Kilowatt Range," Proceedings of the 23rd International Congress on Applications of Lasers and Electro-Optics (2004).

Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).

"Bladeless Trocars," by Johnson & Johnson, http://www.injgateway.com (date of first publication unknown).

Yeh, R. et al., "Microelectromechanical Components for Articulated Microrobots" (date of first publication unknown).

Xu, Q. et al., "Micrometre-scale silicon electro-optic modulator," Nature, vol. 435, pp. 325-327 (May 19, 2005).

Park, H. et al., "Development of Double-Sided Silicon Strip Position Sensor," 2005 IEEE Nuclear Science Symposium Conference Record, pp. 781-785 (2005).

Hammond, S.W., "Architecture and Operation of a Systolic Sparse Matrix Engine," Proceedings of the 3rd SIAM Conference on Parallel Processing for Scientific Computing, pp. 419-423 (1987).

Ra, H. et al., "Biomedical Optics & Medical Imaging—Microtechnology enables endoscopic confocal microscopy," SPIE (http://spie.org) (2007).

International Search Report issued regarding International Application No. PCT/US2007/078868 (Mar. 28, 2008).

PCT, International Search Report, PCT/US2008/056589 (Jul. 30, 2008).

PCT, International Search Report, PCT/US2008/059231 (Jul. 4, 2008).

PCT, International Search Report, PCT/US2007/087923 (May 21, 2008).

PCT, International Search Report, PCT/US2008/056596 (Jun. 23, 2008).

PCT, International Search Report, PCT/US2008/059235 (Jul. 14, 2008).

PCT, International Search Report, PCT/US2007/087930 (Jul. 3, 2008).

PCT, International Search Report, PCT/US2008/051274 (Jul. 18, 2008).

PCT, International Search Report, PCT/US2008/066552 (Oct. 23, 2008).

Invitation to Pay Additional Fees with Partial International Search Report, PCT/US2008/074275 (Jan. 16, 2009).

Invitation to Pay Additional Fees with Partial International Search Report, PCT/US2008/074273 (Dec. 30, 2008).

* cited by examiner

COMBINED SBI AND CONVENTIONAL IMAGE PROCESSOR

TECHNICAL FIELD

The present invention relates generally to systems, devices, and methods for rendering Scanned Bean Imager (SBI) and Focal Plane Array (FPA) image data into a common format for display on a high resolution monitor and storage on a common system.

BACKGROUND OF THE INVENTION

Many medical devices have visual screens for providing real-time data. While some have simple backlit 80×25 text screens, others require television screens or video monitors for displaying video images. The space in hospital operating room environments is very tight and cannot accommodate much equipment, especially bulky video monitors. The space close to a patient, where one or more physicians might operate, is more or less constrained by the geometry of the patient and the need or desire to have certain medical instruments in fixed locations, e.g., anesthesia devices near the patient's head region. Usable space near a patient, especially that which is directly accessible by the operating physician, is at a premium. When multiple medical devices each require a video monitor, the situation presents both space and ergonomic challenges to the physician and support staff as they attempt to coordinate the use of multiple video monitors. In some cases, it might be impracticable to accommodate more than one monitor near the patient. There is therefore a need for a system and method to allow physicians and support staff to use, and coordinate the use of, multiple imaging devices on a common monitor and storage system.

Imaging devices can have different native resolutions and frame rates. Focal Plane Array (FPA) devices typically use Charge Coupled Device (CCD) technology to capture an entire image, or frame, all at once. Typically, these CCD-type imagers capture 30 frames per second (fps). As the frame is rendered to a suitable video format for display on a monitor, the frame may be split into two interlaced (every other line) 60 fps frames that combined make up one full frame on the monitor. This interlacing tends to result in image degradation, but does have the advantage that common inexpensive equipment that supports interlaced video is ubiquitously available and interconnections between various pieces of equipment are relatively simple and straightforward. Alternatively, the FPA may present a progressive scan video signal, whereby each frame is imaged line by line in its entirety resulting in better clarity video. Progressive scan FPA devices and monitors tend to be somewhat more expensive than interlaced devices.

Scanned Beam Imaging (SBI) devices, on the other hand, use a different, higher resolution technology. Instead of acquiring the entire frame at once, the area to be imaged is rapidly scanned point-by-point by an incident beam of light, the reflected light being picked up by sensors and translated into a native data stream representing a series of points and values. SBI technology is especially applicable to endoscopes because SBI devices have better image resolution and present higher quality images of small internal structures, use reduced power light sources, and can be put in very small package diameters for insertion into a human body.

Scanning beam imaging endoscopes using bi-sinusoidal and other scanning patterns are known in the art; see, for example U.S. Patent Application US 2005/0020926 A1 to Wikloff et al. An exemplary color SBI endoscope has a scanning element that uses dichroic mirrors to combine red, green, and blue laser light into a single beam of white light that is then deflected off a small mirror mounted on a scanning bi-axial MEMS (Micro Electro Mechanical System) device. The MEMS device scans a given area with the beam of white light in a pre-determined bi-sinusoidal or other comparable pattern and the reflected light is sampled for a large number of points by red, green, and blue sensors. Each sampled data point is then put in a native SBI data format and transmitted to an image processing device.

While reading data out from FPA/CCD devices is normally performed in an orderly line-by-line manner that makes conversion to a standard video signal relatively straightforward, MEMS-based scanners using bi-sinusoidal or other non-standard scanning patterns result in an ordering of the SBI data that would be incompatible for direct use with ordinary monitors. Also, the image may be scanned at frame rates that ordinary monitors are not capable of refreshing on their screens. To display on an ordinary monitor, the scanned image is therefore first reassembled from the SBI digital pixel image data into a full frame image. This reassembling process is sometimes referred to as rasterization, because a raster or frame is created from the raw data. The image processing device then uses the full frame image to render an appropriate video signal to be displayed on a video monitor at a suitable frame rate.

A native SBI image has potentially superior digital pixel density and dynamic range than an FPA image. Preferentially, the SBI image should be displayed on a monitor suitable for directly displaying the SBI image from the SBI image data. Alternatively, the SBI image data should be converted to a format suitable for display on a high resolution video monitor. There is therefore a need for a system and method to allow physicians and support staff to use, and coordinate the use of, both FPA and SBI imaging devices on a common high resolution monitor and storage system.

SUMMARY OF THE INVENTION

The present invention meets the above and other needs. An apparatus that is a combined SBI and FPA image processor comprises a frame grabber for digitizing video from the legacy FPA devices, a frame mapper for rendering or mapping the FPA video into the SBI digital format, an input selector for selecting which imaging device to display on the high resolution monitor, an SBI processor for storing and processing each frame of SBI video, and a video output encoder for converting the each digitized SBI frame into a video signal appropriate for display on the high resolution monitor. The apparatus allows multiple FPA and SBI imaging devices to use a common high resolution monitor and archive device without increasing or significantly changing the footprint of existing devices in the operating room environment.

The method of the invention involves using the combined SBI and FPA image processor to render both FPA and SBI inputs from imaging devices to a common high resolution format for display on a high resolution monitor and archiving in a storage means.

BRIEF DESCRIPTION OF THE DRAWINGS

The accompanying figures depict multiple embodiments of the combined SBI and FPA image processor. A brief description of each figure is provided below. Elements with the same reference numbers in each figure indicate identical or functionally similar elements. Additionally, as a convenience, the left-most digit(s) of a reference number identifies the drawings in which the reference number first appears.

DETAILED DESCRIPTION

Figure 1:
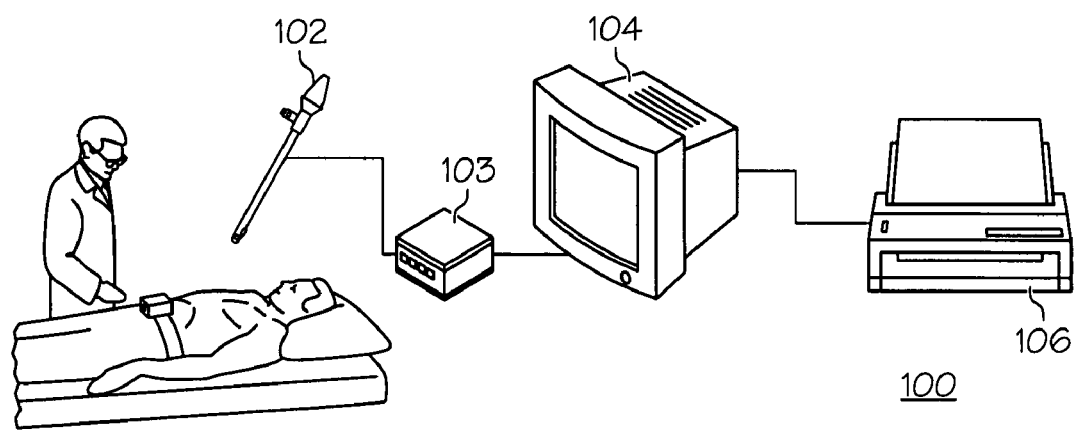
FIG. 1 is a schematic diagram of a prior art imaging system using a Focal Plane Array (FPA) imaging device, a television monitor, and a printer.

FIG. 1 details the prior art imaging systems. Exemplary embodiments of the present invention are detailed in FIGS. 2-5. FIG. 6 illustrates the SBI to FPA conversion process.

Prior Art Imaging System

Referring now to the schematic diagram of a prior art imaging system 100 depicted in FIG. 1, an FPA imaging device 102 connects to an FPA video processor 103 that connects to a monitor 104 that connects to a storage means 106.

In a typical prior art imaging system 100, like that found in a typical hospital operation room, an FPA imaging device 102, usually a CCD-type camera, provides a video signal and, optionally, exchanges control signals or commands with a matching FPA video processor 103 that creates a variety of standard video outputs to the monitor 104. The video signal supplied to the monitor can be a composite signal, an S-Video signal, a Digital Video Interface (DVI) signal, an HDMI signal, or more commonly a component RGB signal, with each of the Red, Green, and Blue signals carried on individual cables and having separate physical connectors for attaching to the monitor 104. The monitor 104 displays the image seen by the FPA imaging device 102 to the physician. The storage means 106, also receives the video signal and allows the physician to record the images the physician is seeing. Typically, the storage means 106 receives the video signal directly from the FPA video processor 103. The storage means 106 can be a printer, an analog VCR, a DVD recorder, or any other recording means as would be known in the art.

Imaging System Using the Combined SBI and FPA Image Processor

Figure 2:
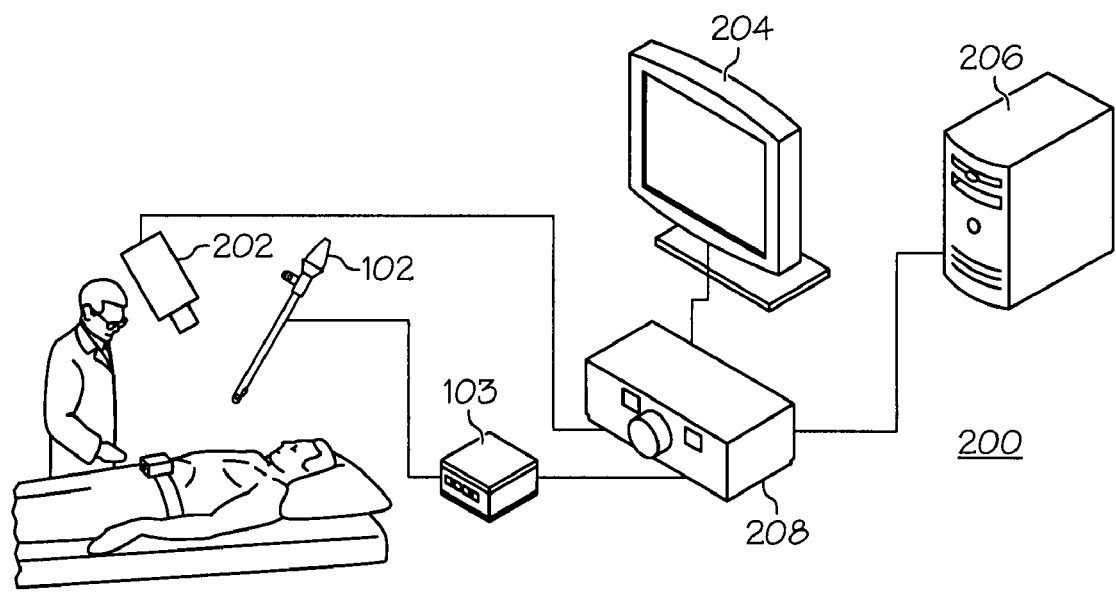
FIG. 2 is a schematic diagram of an embodiment of the invention where both an FPA imaging device and a Scanned Beam Imaging (SBI) imaging device connect to the combined SBI and FPA image processor, and the image processor provides outputs to the high resolution monitor and the archive device.

Referring now to the schematic diagram of an embodiment of an imaging system using the combined SBI and FPA Image Processor System 200 depicted in FIG. 2. An SBI imaging device 202 connects directly to the image processor 208 and an FPA imaging device 102 connects to the image processor 208 through an FPA video processor 103. The image processor 208 connects to both the high resolution pixel-oriented monitor 204 and the pixel-oriented archive device 206.

In the combined SBI and FPA Image Processor System 200, the SBI imaging device 202 delivers SBI digital sample data to the image processor 208, while the FPA imaging device 102 provides a traditional raster video signal through the FPA video processor 103 to the image processor 208. The image processor 208 allows the physician to select which source to display on the high resolution pixel-oriented monitor 204. The image processor 208 sends a separate output to the pixel-oriented archive device 206. The output to the pixel-oriented archive device 206 is controlled by the physician. The physician uses a separate selection control on the endoscope to cause still images to be stored to the pixel-oriented archive device 206, or to start and stop storage of video images to the pixel-oriented archive device 206, allowing the physician the ability to record continuous video or discrete images from the previously selected source. The pixel-oriented archive device 206 can be storage system capable of storing analog data, such as a VCR, or DVD recorder, or it can be a digital device such as a printer or computer system, or any other recording means as would be known in the art.

In an alternate embodiment, the output to the pixel-oriented archive device 206 is a mirror copy of what the physician sees on the high resolution pixel-oriented monitor 204. In another embodiment, the output to the pixel-oriented archive device 206 can be both the SBI imaging device 202 digital sample data and the SBI encoded FPA imaging device 102 video images, including a separate flag indicating which device was selected for viewing on the high resolution pixel-oriented monitor 204 by the physician at the time. In another embodiment, the image processor 208 is capable of multiple inputs from more than two different imaging devices. Various other arrangements are possible for the image processor 208, the pixel-oriented archive device 206, and different kinds of imaging devices, and would be apparent to one having ordinary skill in the art. The figures and descriptions represent merely exemplary embodiments of the invention, and are meant to be limited only by the claim scope.

SBI/FPA Image Processor with Analog and Digital Interfaces

Figure 3:
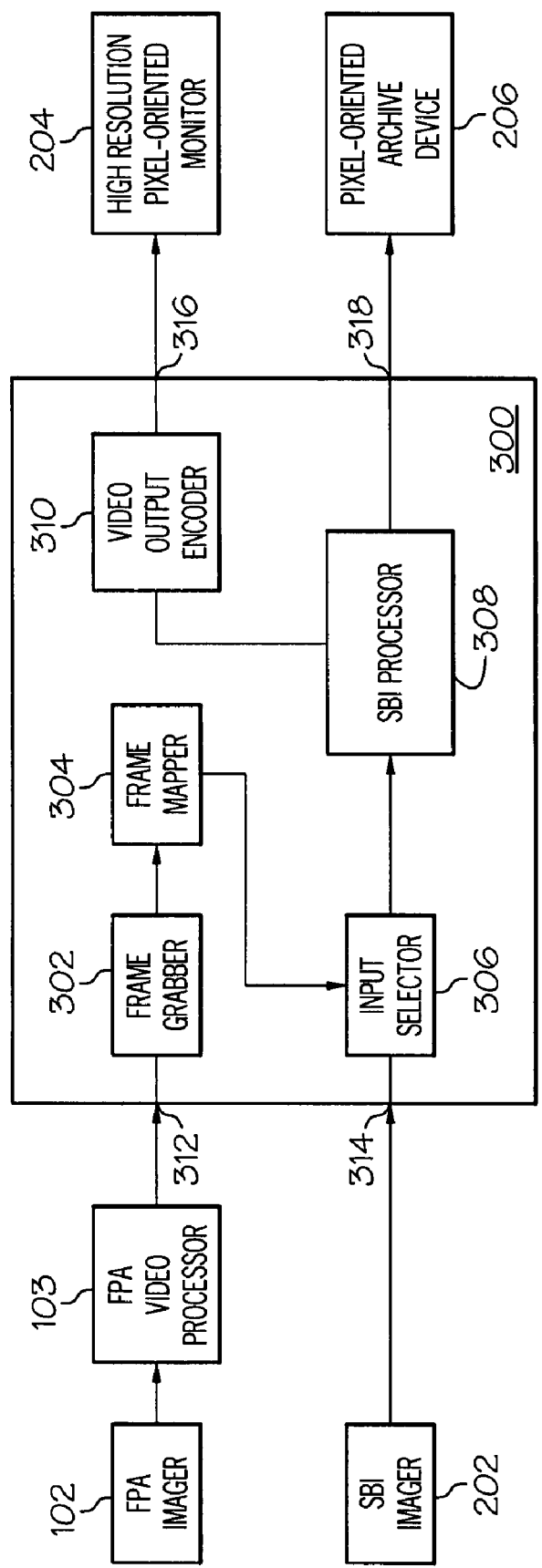
FIG. 3 is a schematic diagram of an embodiment of the combined SBI and FPA image processor showing an FPA frame grabber, an FPA-to-SBI frame mapper, an input selector, an SBI frame rasterizing element, and a video output encoder.

Referring now to the schematic diagram of an SBI/FPA Image Processor with Analog and Digital Interfaces 300 depicted in FIG. 3, an FPA imaging device 102 is connected through an FPA video processor 103 to a pixel-oriented video input 312 which is connected to a video frame grabber 302. The video frame grabber 302 connects to a frame mapper 304 which connects to an input selector 306. The input selector 306 is also connected to the SBI input 314 that is connected to an SBI imaging device 202. The input selector 306 connects to an SBI processor 308. The SBI processor 308 connects to both the pixel-oriented storage means output 318 and the video output encoder 310. The video output encoder 310 further connects to the pixel-oriented video monitor output 316. The pixel-oriented video monitor output 316 connects to the high resolution pixel-oriented monitor 204. The pixel-oriented storage means output 318 connects to the pixel-oriented archive device 206.

An embodiment of the SBI/FPA Image Processor with Analog and Digital Interfaces 300 has inputs for accepting both analog and digital video devices. The pixel-oriented video input 312 accepts RGB video inputs from an FPA video processor 103 that is connected to an FPA imaging device 102. The frame grabber 302 decodes the RGB video signal and digitizes each video frame. A frame mapper 304 uses the digitized video frame to encode a new SBI formatted digital sample data stream, thereby rendering or mapping the original video signal from the pixel-oriented video input 312 to the SBI format. The frame mapper 304 assigns each FPA pixel from the frame grabber 302 in a prescribed manner to create each sample of a synthesized SBI formatted digital sample stream. In this process a portion of each FPA pixel's color value is assigned to one or more SBI sample stream locations. The frame mapper 304 presents the SBI compatible digital sample data stream to the input selector 306. The input selector 306 also receives an input from the SBI input 314. The SBI input 314 accepts an SBI digital sample data stream from an SBI imaging device 202.

The input selector 306 allows the physician to select which of the two devices to display on the high resolution pixel-oriented monitor 204. The input selector 306 can be controlled using a switch on the image processor 208. Based on the physician's device selection, the input selector 306 sends one of the two SBI digital sample data streams to the SBI processor 308. The SBI processor 308 takes the SBI digital sample data stream and maps the individual pixel data points into an high resolution video frame. The SBI processor 308 performs color correction, contrast and gamma control, and other imaging enhancing algorithms on the video data. The SBI processor 308 can enhance the image differently depending upon whether the original image is from an FPA or an SBI imaging device.

The video output encoder 310 uses the mapped video frame in the SBI processor 308 to encode a suitable video output signal for driving the high resolution pixel-oriented monitor 204 and presents it to the pixel-oriented video monitor output 316. The video output signal preferably uses either a progressive scan 720 HDMI (ITU-R BT.601) with a 60 fps refresh rate or an SVGA VESA-compatible output using at least 800×600 pixel resolution and 72 fps refresh rate, although both higher and lower resolutions and refresh rates are contemplated. Typically, a compatible commercially available medical grade display will be used, such as the Dynamic Displays' MD1518-101 display or any other suitable display as would be known by one having ordinary skill in the art. Pixel-oriented output from the SBI processor 308 sent to the pixel-oriented archive device 206 via the pixel-oriented storage means output 318 is controlled by the physician. The physician uses a selection control on the endoscope to select which images from the SBI processor 308 to store to the pixel-oriented archive device 206, allowing the physician the ability to record continuous video or discrete images. The pixel-oriented archive device 206 can be storage system capable of storing analog data, such as a VCR, or DVD recorder, or it can be a digital device such as a printer or computer system, or any other recording means as would be known in the art.

The video frame grabber 302, frame mapper 304, input selector 306, SBI processor 308, and video output encoder 310 modules of the SBI/FPA Image Processor with Analog and Digital Interfaces 300 are implemented using one or more microcontroller processors (which may be independently applied or embedded in an ASIC or FPGA), and may also include one or more discrete electronic support chips. The actual circuit implementation necessary to perform the digital signal processing necessary for color correction, dynamic range control, data mapping and other pixel manipulation processes could be done in a variety of ways that would be obvious to one of ordinary skill in the art.

In another embodiment of the invention, the SBI digital sample data stream from the SBI processor 308 is sent to an SBI archive device 404 via an SBI digital storage means output 408. In another embodiment of the invention, the analog video inputs from the FPA video processor 103 can be composite, S-Video, or other component interfaces including xVGA, and can be in NTSC, PAL, SECAM, VESA or other formats. In another embodiment of the invention, the video inputs from the FPA video processor 103 can be digital, including, but not limited to, the DVI, HDMI, or DV MPEG 4:2:2 standards. In these embodiments, the frame grabber 302 would be suitably adapted to handle the other formats, acquiring the video frame by digitizing if it is an analog video signal, or acquiring the video frame by capturing the digital data if it is a digital video signal. In another embodiment the high resolution pixel-oriented monitor 204 could be a heads up display worn by the physician.

SBI/FPA Image Processor with SBI Digital Sample Data Output

Figure 4:
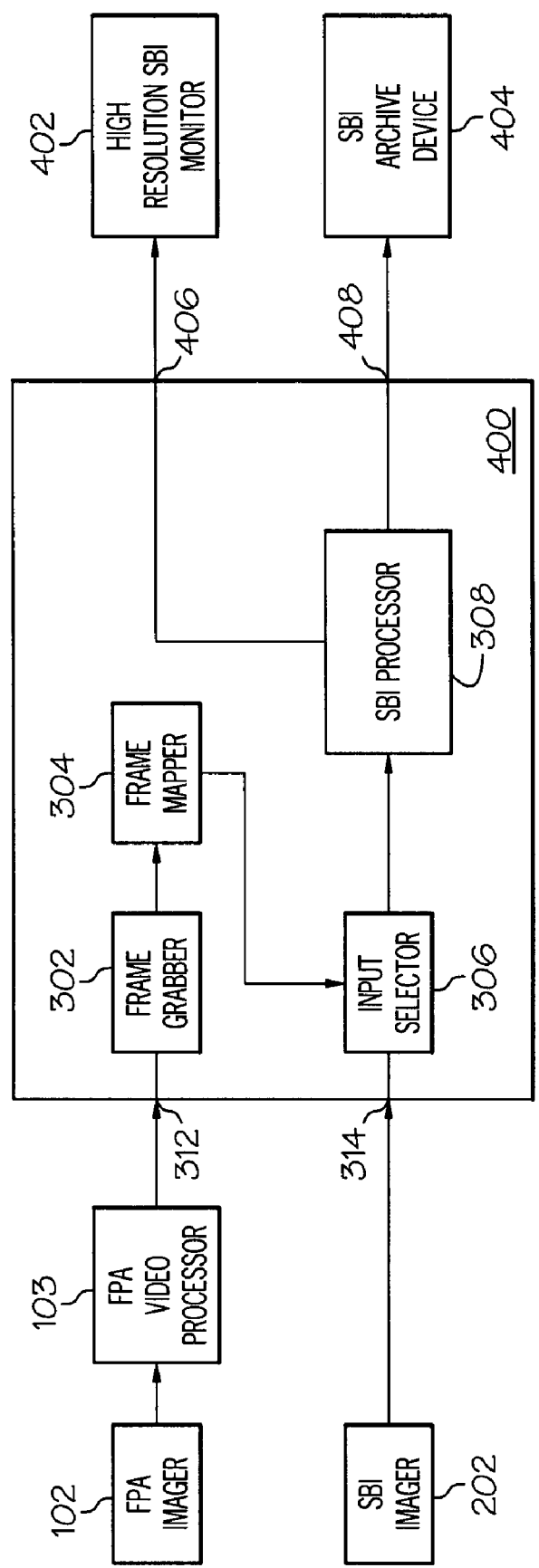
FIG. 4 is a schematic diagram of an alternate embodiment of the combined SBI and FPA image processor, where the selected SBI digital pixel input is sent to the monitor and archive device without rasterizing the frame.

Referring now to the schematic diagram of an SBI/FPA Image Processor with SBI Digital Sample Data Output 400 depicted in FIG. 4, an FPA imaging device 102 is connected through an FPA video processor 103 to a pixel-oriented video input 312 which is connected to a video frame grabber 302. The video frame grabber 302 connects to a frame mapper 304 which connects to an input selector 306. The input selector 306 is also connected to the SBI input 314 that is connected to an SBI imaging device 202. The input selector 306 connects to an SBI processor 308. The SBI processor 308 connects to both the SBI video monitor output 406 and the storage means output 408. The SBI storage means output 408 connects to the SBI archive device 404. The SBI video monitor output 406 connects to the high resolution SBI monitor 402.

An embodiment of the SBI/FPA Image Processor with SBI Digital Sample Data Output 400 has inputs for accepting both analog and digital video devices. The pixel-oriented video input 312 accepts RGB video inputs from an FPA video processor that is connected to an FPA imaging device 102. The frame grabber 302 decodes the RGB video signal and digitizes each video frame. A frame mapper 304 uses the digitized video frame to encode a new SBI formatted digital sample data stream, thereby rendering or mapping the original video signal from the pixel-oriented video input 312 to the SBI format. The frame mapper 304 assigns each FPA pixel from the frame grabber 302 in a prescribed manner to create each sample of a synthesized SBI formatted digital sample stream. In this process a portion of each FPA pixel's color value is assigned to one or more SBI sample stream locations. The frame mapper 304 presents the SBI compatible digital sample data stream to the input selector 306. The input selector 306 also receives an input from the SBI input 314. The SBI input 314 accepts an SBI digital sample data stream from an SBI imaging device 202. The input selector 306 allows the physician to control which of the two devices to display on the high resolution SBI monitor 402. The input selector 306 can be controlled using a switch on the image processor 208. Based on the physician's device selection, the input selector 306 sends one of the two SBI digital sample data streams to the SBI processor 308. The SBI processor 308 performs color correction, contrast and gamma control, and other imaging enhancing algorithms on the video data. The SBI processor 308 can enhance the image differently depending upon whether the original image is from an FPA or an SBI imaging device.

The SBI processor 308 presents the SBI digital sample data stream to the SBI video monitor output 316 which is connected to a high resolution SBI monitor 402 capable of accepting an SBI signal input. The output from the SBI processor 308 sent to the SBI archive device 404 via the SBI storage means output 408 is controlled by the physician. The physician uses a separate selection control on the endoscope to select which images from the SBI processor 308 to store to the SBI archive device 404, allowing the physician the ability to record continuous video or discrete images. The SBI storage means output 408 is a digital device such as a printer or computer system, or any other recording means as would be known in the art.

The video frame grabber 302, frame mapper 304, input selector 306, SBI processor 308, and video output encoder 310 modules of the SBI/FPA Image Processor with SBI Digital Sample Data Output 400 are implemented using one or more microcontroller processors (which may be independently applied or embedded in an ASIC or FPGA), and may also include one or more discrete electronic support chips. The actual circuit implementation necessary to perform the digital signal processing necessary for color correction, dynamic range control, data mapping and other pixel manipulation processes could be done in a variety of ways that would be obvious to one of ordinary skill in the art.

In alternative embodiment of the invention, the analog video inputs from the FPA video processor 103 can be composite, S-Video, or other component interfaces including xVGA, and can be in NTSC, PAL, SECAM, VESA, or other formats. In another embodiment of the invention, the video inputs from the FPA video processor 103 can be digital, including, but not limited to, the DVI, HDMI, or DV MPEG 4:2:2 standards. In these embodiments, the frame grabber 302 would be suitably adapted to handle the other formats, acquiring the video frame by digitizing if it is an analog video signal, or acquiring the video frame by capturing the digital data if it is a digital video signal. In another embodiment the high resolution SBI monitor 402 could be a heads up display worn by the physician.

Programmable SBI/FPA Image Processor

Figure 5:
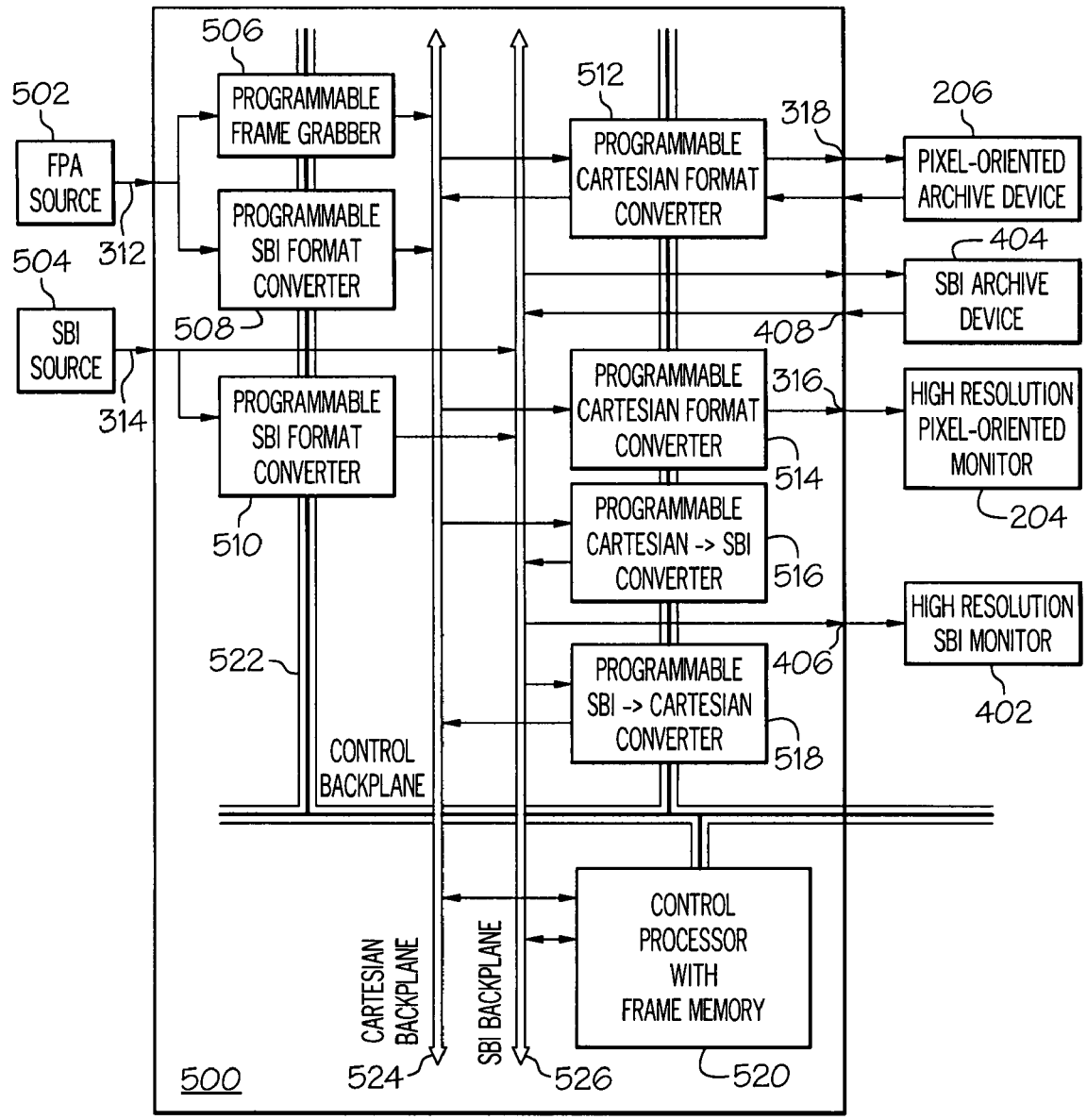
FIG. 5 is a schematic diagram of an alternate embodiment of the combined SBI and FPA image processor, where the image processor is programmable and can support various Cartesian frame-based inputs and outputs as well as digital pixel stream inputs and outputs.
Figure 6:
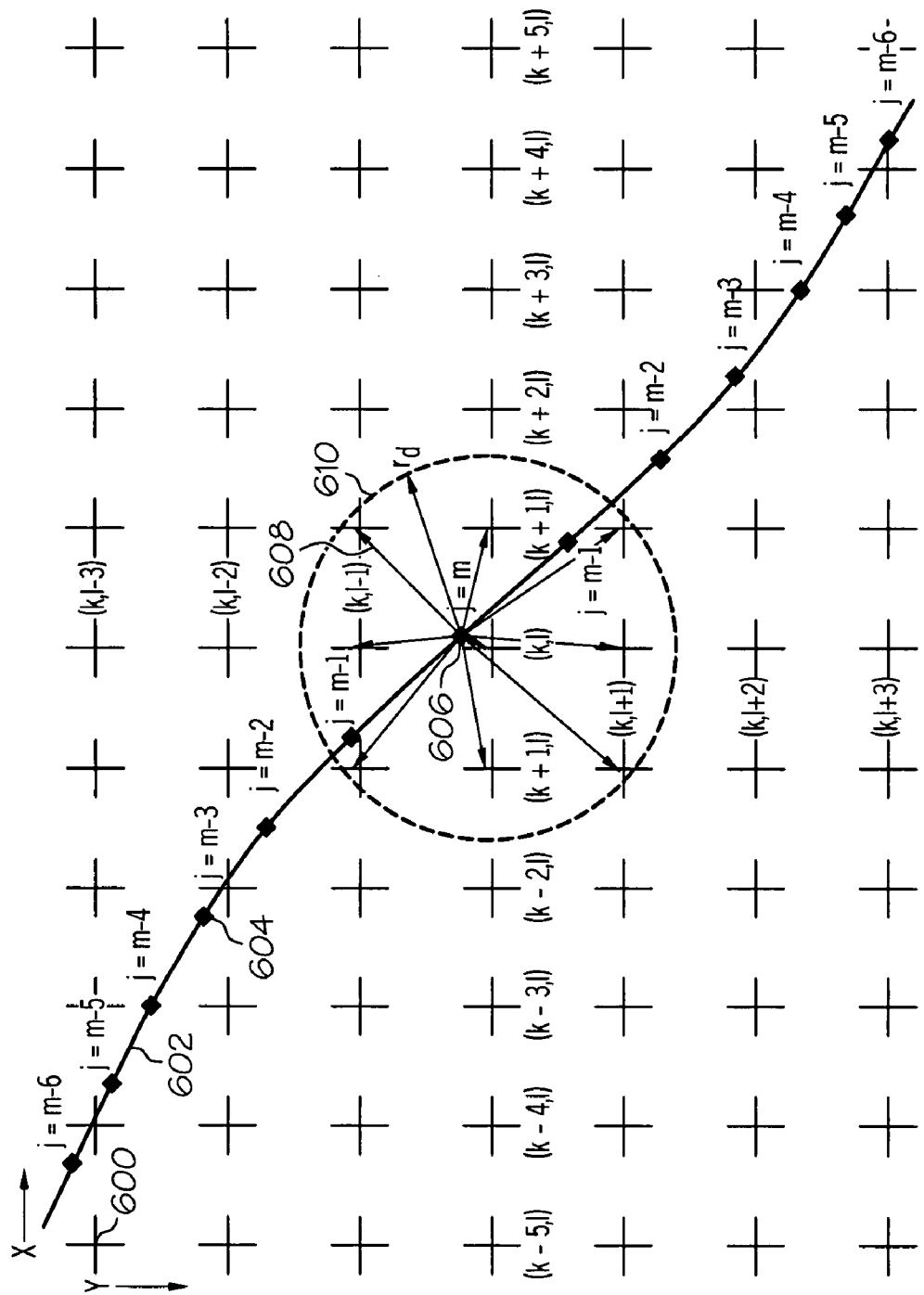
FIG. 6 is an illustration used to facilitate understanding the conversion process from the two-dimensional Cartesian space format typical of FPA devices to the pixel stream format used by SBI devices.

Referring now to the schematic diagram of a programmable SBI/FPA Image Processor 500 depicted in FIG. 5, a pixel-oriented video input 312 connects an FPA source 502 to both a programmable frame grabber 506 and a programmable digital format converter 508 which connect internally to a Cartesian backplane 524. The Cartesian backplane 524 connects to a programmable digital format converter 512 that connects to the pixel-oriented archive device 206 through the pixel-oriented storage means output 318. The Cartesian backplane 524 further connects to a programmable Cartesian format converter 514 that connects to the high resolution pixel-oriented monitor 204 through the pixel-oriented video monitor output 316. The Cartesian backplane 524 further connects to a control processor with frame memory 520, a programmable Cartesian to SBI converter 516, and a programmable SBI to Cartesian converter 518. The control processor with frame memory 520, the programmable Cartesian to SBI converter 516, and the programmable SBI to Cartesian converter 518 also connect to an SBI backplane 526. The SBI backplane 526 connects to an SBI source 504 through an SBI input 314. The SBI backplane 526 also connects to the SBI input 314 through a programmable SBI format converter 510. The SBI backplane 526 further connects to an SBI archive device 404 through an SBI storage means output 408, and a high resolution SBI monitor 402 through an SBI video monitor output 406. A control backplane 522 connects the control processor with frame memory 520 to the programmable frame grabber 506, the programmable digital format converter 508, the programmable SBI format converter 510, the programmable digital format converter 512, the programmable Cartesian format converter 514, the programmable Cartesian to SBI converter 516, and the programmable SBI to Cartesian converter 518.

An embodiment of the Programmable SBI/FPA Image Processor 500 has inputs for accepting either or both analog and digital video devices. The pixel-oriented video input 312 accepts video inputs from an FPA source 502. The FPA source 502 can be analog in which case the pixel-oriented video input 312 can be composite, S-Video, or other component interfaces including xVGA, and can be in NTSC, PAL, SECAM, VESA, or other formats. The pixel-oriented video input 312 can also be a digital interface for accepting DVI, HDMI, or DV MPEG 4:2:2 inputs from a digital FPA source 502.

The programmable frame grabber 506 acquires the analog video signal from an analog FPA source 502 by digitizing each video frame into an internal pixel-oriented format and transfers each frame of video to the control processor with frame memory 520 across the Cartesian backplane 524. The programmable digital format converter similarly acquires a digital video signal from a digital FPA source 502 by converting the encoded frames of video into an internal pixel-oriented format and transfers each frame of video to the control processor with frame memory 520 across the Cartesian backplane 524.

The programmable SBI format converter 510 decodes an SBI source 504 input into an internal SBI format and transfers the digital data stream to the control processor with frame memory 520. Alternatively, the SBI source 504 can transfer the SBI formatted digital sample data stream directly to the control processor with frame memory 520 if it is already in the internal SBI format.

Once the pixel-oriented frame of video or SBI formatted digital sample data stream starts to transfer to the control processor with frame memory 520 it can start performing color correction, contrast and gamma control, and other imaging enhancing algorithms on the video data. Because SBI data samples can have greater resolution or include sampling of spectrum outside of the normal Red Green and Blue colorspace, the control processor with frame memory 520 may enhance the image differently depending upon whether the original image is from an FPA or an SBI imaging device. As an illustration only, if the SBI data samples include sampling of how much the imaged area fluoresced when an incident beam shone on it, the control processor with frame memory 520 may highlight the area in an normally absent color such as bright green, or it could utilize an edge detection algorithm and draw a flashing bright white line around the perimeter of the area. If the area being imaged by the SBI source 504 contained a greater depth of colors than could be displayed on a high resolution pixel-oriented monitor 204, the control processor with frame memory 520 could scale the intensity linearly or non-linearly to optimal levels for display. The control processor with frame memory 520 can also use data from previous frames or scans in enhancing the current video data. These and other image enhancing algorithms known to those having ordinary skill in the art could be utilized.

The control processor with frame memory 520 uses the control backplane 524 to control which of the input devices, 502, 504, to use as input, and which type of high resolution monitor, 204, 402, to use for displaying the video. In an alternate embodiment the high resolution pixel-oriented monitor 204 or high resolution SBI monitor 402 could be a heads up display worn by the physician. The control processor with frame memory 520 also controls which images to send to the archive devices, 206, 404 and whether the archive device is to record continuous video or discrete images. The archive devices, 206, 404 can be either analog or digital storage devices.

The programmable SBI/FPA Image Processor 500 can run in four different modes: FPA source to SBI monitor mode;

FPA source to pixel-oriented monitor mode, SBI source to pixel-oriented monitor mode; and SBI source to SBI monitor mode.

FPA Source to SBI Monitor Mode

In FPA source to SBI monitor mode, the control processor with frame memory 520 forwards the pixel-oriented frame of video across the Cartesian backplane 524 to the programmable Cartesian to SBI converter 516. The programmable Cartesian to SBI converter 516 converts the pixel-oriented video frame to an SBI formatted digital sample data stream, thereby rendering or mapping the original video signal from the FPA source 502 to the SBI format. The programmable Cartesian to SBI converter 516 assigns each FPA pixel from the frame in a prescribed manner to create each new sample of the synthesized SBI formatted digital sample stream. In this process a portion of each FPA pixel's color value is assigned to one or more SBI sample stream locations. The control processor with frame memory 520 can then store the SBI formatted digital sample data stream back in memory, perform additional processing, or direct the SBI formatted digital sample data stream across the SBI backplane 526 to the high resolution SBI monitor 402 or the SBI archive device 404.

FPA Source to Pixel-Oriented Monitor Mode

In FPA source to pixel-oriented monitor mode, the control processor with frame memory 520 forwards pixel-oriented frame of video across the Cartesian backplane 524 to the programmable Cartesian format converter 514, which puts the frame of video into the appropriate analog or digital format for display on the high resolution pixel-oriented monitor 204. If the high resolution pixel-oriented monitor 204 is analog, the pixel-oriented video monitor output 316 can be composite, S-Video, or other component interfaces including xVGA, and can be in NTSC, PAL, SECAM, VESA, or other formats. If the high resolution pixel-oriented monitor 204 is digital, the pixel-oriented video monitor output 316 can be a digital interface for accepting DVI, HDMI, DV or other digital connections. The control processor with frame memory 520 can also direct the programmable digital format converter 512 to send the current frame of video on the Cartesian backplane 524 to the pixel-oriented archive device 206.

SBI Source to Pixel-Oriented Monitor Mode

In SBI source to pixel-oriented monitor mode, the control processor with frame memory 520 forwards the SBI digital sample data stream across the SBI backplane 526 to the programmable SBI to Cartesian converter 518. The programmable Cartesian to SBI converter 518 converts the SBI digital sample data stream to a pixel-oriented video frame, thereby rendering or mapping the original video signal from the SBI source 504 to the pixel-oriented format. The programmable SBI to Cartesian converter 518 assigns each SBI formatted sample to one or more FPA pixels in a prescribed manner to create each new sample of the synthesized pixel-oriented frame. In this process a portion of each SBA data sample's color value is assigned to one or more FPA pixels. The control processor with frame memory 520 can then store the pixel-oriented frame of video back in memory, perform additional processing, or direct the pixel-oriented frame of video across the Cartesian backplane 524 to the programmable Cartesian format converter 514, which puts the frame of video into the appropriate analog or digital format for display on the high resolution pixel-oriented monitor 204. The control processor with frame memory 520 can also direct the programmable digital format converter 512 to send the current frame of video on the Cartesian backplane 524 to the pixel-oriented archive device 206.

SBI Source to SBI Monitor Mode

In SBI source to SBI monitor mode, the control processor with frame memory 520 can have both the high resolution SBI monitor 402 and the SBI archive device 404 use the current SBI formatted digital sample stream from the SBI source 504 present on SBI backplane 526. Alternatively, the control processor with frame memory 520 can store the SBI formatted digital sample data stream from the SBI source 504 in memory, perform additional processing, and then direct the modified SBI formatted digital sample stream back on the SBI backplane 526 to the high resolution SBI monitor 402 and the SBI archive device 404.

Processor and Backplane Architecture

The control processor with frame memory 520, the programmable frame grabber 506, the programmable digital format converter 508, the programmable SBI format converter 510, the programmable digital format converter 512, the programmable Cartesian format converter 514, the programmable Cartesian to SBI converter 516, and the programmable SBI to Cartesian converter 518 modules of the programmable SBI/FPA Image Processor with SBI Digital Sample Data Output 500 are implemented using one or more microcontroller processors (which may be independently applied or embedded in an ASIC or FPGA), and may also include one or more discrete electronic support chips. The actual circuit implementation necessary to perform the digital signal processing necessary for color correction, dynamic range control, data mapping and other pixel manipulation processes could be implemented in circuitry and software in a variety of ways that would be obvious to one of ordinary skill in the art.

The control backplane 522, the Cartesian backplane 524, and the SBI backplane 526 can be discrete backplanes or they can be logical backplanes running on a common physical backplane. Backplane technology is a well developed art and the backplanes could be implemented in circuitry and software in a variety of ways that would be obvious to one of ordinary skill in the art.

Converting Between SBI Formatted Data Streams and Pixel-Oriented Video Frames

The dual resonant scanned beam imager is a class of MEMS oscillating mirror imagers with two orthogonal axis of rotation (labeled x and y) that operate in a resonant mode. By convention, the x-axis oscillation is referred to as the fast axis and the y-axis oscillation is referred to as the slow axis. When properly excited, the oscillating mirror causes a beam of light reflected from its surface to trace a geometric pattern known as a Lissajous figure or pattern. Based on the phase relationship of the slow and fast axis oscillation, the basic Lissajous pattern can precess. The number of slow axis cycles required to precess the pattern to an initial spatial point, is called the interleave factor.

$$x(t)=A\sin(w_f t+\phi_f)$$

$$y(t)=B\cos(w_s t+\phi_s)$$

The Lissajous pattern traced by an SBI is spatially repeated after a set number of oscillations on the slow axis (interleave factor). Once a reference point on the complete set of Lissajous patterns is identified, one can view the constant sample time, digital data stream captured at each optical detector as a vector of constant length, the SBI Data Vector (SDVi). The number of samples in the vector (N) is equal to the interleave factor times the period of the slow axis oscillation divided by the sample interval (ts).

$$SDV_i(j\Delta t)=[s(i,j)]_{j=0}^{N-1}$$

If there are multiple optical detectors sampled coincidently, then the SBI data stream can be viewed as a matrix, the SBI Data Matrix (SDM), that has a row count equal to the number of sampled detectors (M) and a column count equal to the number of samples in each SDV (N). For example, a system of comprising RGB channels plus an additional Fluorescence channel would be as follows.

$$SDM = \begin{bmatrix} SDV_R \\ SDV_G \\ SDV_B \\ SDV_F \end{bmatrix}$$

The pixel-oriented video frame is represented as a pixel data matrix (PDM), a two-dimensional matrix with row and column indices that represent the display space. A typical system might have 600 rows (Y) and 800 columns (X). Each point in the data set is a triple representing red (R), green (G), and blue (B) display intensities.

$$PDM = \begin{bmatrix} (r_{0,0}, g_{0,0}, b_{0,0}) & \cdots & (r_{0,799}, g_{0,799}, b_{0,799}) \\ \vdots & & \vdots \\ (r_{599,0}, g_{599,0}, b_{599,0}) & & (r_{799,599}, g_{799,599}, b_{799,599}) \end{bmatrix}$$

In order to conveniently describe matrix operations, it is useful to define a view of the matrix, PDM, that is a vector of length XY, and define that vector as PDV.

The transformation from matrix to vector representation can be achieved algorithmically. To transform data from the Lissajous SBI space SDM to the Cartesian pixel-oriented space PDM, a transformation matrix is defined. The transformation matrix is a N×XY matrix where N is the number of samples in the SDV; X is the number of horizontal pixels in the Cartesian pixel-oriented space; Y is the number of vertical pixels in the Cartesian pixel-oriented space.

Referring now to FIG. 6 provides a close-up look at the physical situation when converting from the Lissajous space SDM to the Cartesian space PDM. The grey crosses in the imaged area 600 represent the pixels in Cartesian Space mapped with the matrix origin located in the upper left hand corner. Each pixel is represented by conventional Cartesian coordinates (x,y). The solid line is the SBI beam path 602 and represents a portion of a specific trajectory of the dual resonant scanned beam through the imaged area 600. The black diamonds indicate SBI samples 604 taken along that SBI beam path 602. The SBI sample index (j) increases from the top left to bottom right in this depiction. The trajectory of the SBI beam path 602 (with increasing sample index) can be in any direction through a subset of the imaged area 600. Note that in FIG. 6 the SBI samples 604 at the top left and bottom right are closer together than the SBI samples 604 in the center of the figure. This difference is shown to reinforce the implications of a constant data-sampling rate applied to resonant (sinusoidal) beams.

Conversion from Lissajous Space SDM to Cartesian Space PDM

In general, conversion from Lissajous space SDM to the Cartesian space PDM can be represented as the matrix multiplication:

[SDV][T]=[PDV]

If the number of samples in the SDV matrix is N and the size of the Cartesian space is X by Y, then the matrix, SDV, is of dimension 1×N, the transformation matrix, T, is of dimension N by (X*Y) and the matrix PDV, is of dimension 1 by X*Y. In FIG. 6, we are converting from Lissajous space SDM to the Cartesian space PDM for every sample and pixel, but it is instructive for purposes of illustrating the algorithm to concentrate on a single SBI data sample (m) 606.

The object is to distribute the data from the imaged area 600 at sample m 606 to the associated pixels 608 (those within the circle 610) in the pixel space. The following steps can be used to populate the T matrix:

Step 1: Through precise knowledge of the path of the SBI beam (that knowledge is inherent in the scanner drive and positioning system) it is possible to identify the pixel data point closest to the SBI sample, m 606, at $t=m\Delta t_s$ from the start of the frame. We denote that pixel with the indices (k,l).

Step 2: Construct a circle 610 in Cartesian space of radius, $r_d$, over which the data from SBI sample, m 606, is going to be distributed to the associated pixels 608 contained within circle 610.

Step 3: For each associated pixel 608 (k+s,l+t), where s and t are integers that describe points in Cartesian space located within the circle constructed in step 2:

a. Compute the length (in Cartesian space), l, of the vector from the Cartesian space location of the SBI sample, m 606, to the center of the associated pixel 608, (k+s,l+t).

b. Calculate a weighting value, w, that is proportional to the length, of the vector, such as:

$$w = e^{-F \frac{s}{r_d}}$$

where:
w is the weighting factor,
s is the length of the vector from the SBI data point (m) 606 to the associated pixel 608 of interest
F is a controllable constant that sets how fast the effects of the SBI data falls off as the value of l increases.
$r_d$ is the radius of the circle 610 over which the data from the SBI sample is being distributed
Other weighting functions as would be known in the art could also be used.

c. Record the value of w into the transformation matrix T at the x,y location of the subject pixel. The location in the matrix will be at the row m and the column which can be derived using the following mapping equations:

Define a m×n matrix A from which we wish to create a 1×mn vector B. Define the operation with the symbol ↦. Write the mapping as A ↦ B. Conceptually, B is a concatenation of each row of A starting at row 0 and ending at row m−1.

(i) Mathematically, define a function for the conversion of a two-dimensional space to a one-dimensional space:

$j=\Theta(x,y,m,n)$ where
j is an integer offset from the start of a vector (j=0);
x is the traditional display space notion of the horizontal displacement from the origin.
y is the traditional display space notion of the vertical displacement from the origin.
m is the number of rows in the matrix A
n is the number of columns in the matrix A
Use the following instantiation of the function, Θ.

$j=yn+x$ where
x is a positive integer less than m
y is a positive integer less than n (ii) Mathematically, define a set of functions for the conversion of a one-dimensional space into a two-dimensional space:

$x=\Theta_x(j,m,n)$ $y=\Theta_y(j,m,n)$ consistent with equation j=yn+x, use the following instantiation of the functions $\Theta_x, \Theta_y$:

$$x = j \% n$$
$$y = \frac{j - (j \% n)}{n}$$

where % is the modulus operator.

Step 4 (optional): It should be recognized that this method creates a sparse matrix, T. To improve computational efficiency, one can use various methods as are known in the art to create a banded matrix amenable to hardware acceleration or optimized software algorithms.

Conversion from Cartesian Space PDM to Lissajous Space SDM

In general, conversion from Cartesian space PDM to Lissajous space SDM can be represented as a matrix multiplication. In general, one can convert from a imaged area 600 in Cartesian space to a SBI sample vector, m, by solving the matrix equation:

$$[SDV] = \frac{[PDV]}{[T]}$$

The equation yields the multi-bit (analog) scan beam vector, SDV, which would result from a multi-bit (analog) Cartesian space matrix, PDM. Note that in cases where the transformation matrix, T, is not square, the creation of the inverse matrix (the result of, T, being in the denominator) can be computationally challenging. As would be known in the art, linear algebra can be used to accomplish this inversion for rectangular matrices.

Cartesian Frames and FPA Frames

SBI imagers have a wider dynamic range per pixel and generally support more pixels than FPA devices. Therefore, there will not be a one-to-one mapping for each SBI data point to each Cartesian pixel. As would be well known in the art, the conversion process from SBI space to FPA space would therefore be lossy. To decrease loss, especially for image enhancement and storage of raw data purposes, the processor can internally use a much larger Cartesian frame with greater dynamic range than would be output to a monitor or received from an FPA or SBI device, and simply downsample and reduce the dynamic range appropriate to the monitor or storage device prior to outputting the video signal. Such a frame would facilitate a nearly lossless internal conversion between SBI and FPA spaces. It should be noted therefore, that this disclosure contemplates, and the claims should be read in light of, instances where the image processor uses an internal pixel frame that is both equal to, less than, or greater than that of an SBI or FPA pixel-oriented imaging device.

CONCLUSION

The numerous embodiments described above are applicable to a number of different applications. One particular application where the Combined SBI and FPA Image Processor is advantageous is in hospital operating room environments where space near a patient is at a premium and there is no room for multiple monitors, however there are many additional applications that would be apparent to one of ordinary skill in the art.

The embodiments of the invention shown in the drawings and described above are exemplary of numerous embodiments that may be made within the scope of the appended claims. It is contemplated that numerous other configurations of the disclosed system, process, and device for allowing different format imaging devices to use a common high resolution monitor may be created taking advantage of the disclosed approach. It is the applicant's intention that the scope of the patent issuing herefrom will be limited only by the scope of the appended claims.

What is claimed is:

1. An FPA and SBI image processor for FPA and SBI imaging devices, the apparatus comprising:
    a first input port that accepts a first SBI formatted digital sample data stream;
    a second input port that accepts a video signal from an FPA video source;
    an FPA processor that renders the video signal from the FPA video source to a second SBI formatted digital sample data stream;
    a selector that selects an SBI formatted digital sample data stream from the first SBI formatted digital sample data streams and the second SBI formatted digital sample data streams for processing;
    an SBI processor means for generating processed data by processing the selected SBI formatted digital sample data stream; and
    an output port that outputs the processed data.

2. The apparatus of claim 1 further comprising a high resolution monitor adapted to accept the processed data from the output port.

3. The apparatus of claim 2 wherein the high resolution monitor is selected from the group consisting of:
    an SBI compatible monitor; and
    a pixel-oriented FPA compatible monitor.

4. The apparatus of claim 2 where the high resolution monitor is a wearable heads-up display.

5. The apparatus of claim 1 further comprising an archive that accepts the processed data from the output port.

6. The apparatus of claim 5 wherein the archive is selected from the group consisting of:
    an SBI compatible archive; and
    a pixel-oriented FPA compatible archive.

7. The apparatus of claim 1 where the FPA processor further comprises:
    a frame grabber for acquiring an FPA video frame from the video signal; and
    a frame mapper for rendering the FPA video frame into an SBI formatted digital sample data stream.

8. The apparatus of claim 1 where the FPA video source is one selected from the group consisting of:
    the output of an FPA camera;
    the output of a video recording device;
    the output of an FPA video processor; and
    a computer synthesized video stream.

9. An FPA and SBI image processor that allows both FPA and SBI imaging devices to use a common high resolution monitor and archive, the apparatus comprising:
    an input port adapted for accepting a first SBI formatted digital sample data stream;

an input port adapted for accepting a video signal comprised of a first series of pixel-oriented video frames from an FPA video source;

a processor capable of (a) converting the first series of pixel-oriented video frames in the video signal to a second SBI formatted digital sample data stream; (b) rasterizing the first SBI formatted digital sample data stream into a second series of pixel-oriented video frames; (c) selecting a first output from the first SBI formatted digital sample data stream, the second SBI formatted digital sample data streams, the first series of pixel-oriented video frames, and the second series of pixel-oriented video frames; and (d) rendering the first output to a suitable format for the high resolution monitor; and an output port adapted for outputting the first output to the high resolution monitor.

10. The apparatus of claim 9 where the processor is capable of performing image enhancing algorithms on the first SBI formatted digital sample data stream, the second SBI formatted digital sample data streams, the first series of pixel-oriented video frames, and the second series of pixel-oriented video frames.

11. The apparatus of claim 9 where the output port includes circuitry and a physical connector for connecting to a high resolution pixel-oriented FPA monitor.

12. The apparatus of claim 9 where the processor is further capable of (e) selecting a second output from the first SBI formatted digital sample data stream, the second SBI formatted digital sample data streams, the first series of pixel-oriented video frames, and the second series of pixel-oriented video frames; and further comprising:

an archive output port adapted for outputting the second output to the archive device when triggered by a user.

13. The apparatus of claim 12 where the archive output port includes circuitry and a physical connector for connecting to a pixel-oriented archive device.

14. The apparatus of claim 9 where the FPA video source is one selected from the group consisting of:
the output of an FPA camera;
the output of a video recording device;
the output of an FPA video processor; and
a computer synthesized video stream.

15. A method for allowing both an FPA video source and an SBI imaging device to use a common high resolution monitor and archive, the method comprising the steps of:
acquiring, as a first source, a series of pixel-oriented frames of video from the FPA video source;
inputting, as a second source, an SBI formatted digital sample data stream from the SBI imaging device;
selecting, as an output selection, one of the first source and the second source;
outputting the output selection to the high resolution monitor; and
triggering the output selection to be sent to the archive.

16. The method of claim 15, the method further comprising the step:
performing image enhancement processes on the output selection prior to outputting.

17. The method of claim 15, the method further comprising the step:
converting the first source into an SBI format.

18. The method of claim 15, the method further comprising the steps:
rasterizing the second source into a pixel-oriented FPA format; and rendering the output selection to a suitable high resolution FPA video signal for use with the high resolution monitor.

19. An FPA and SBI image processor for FPA and SBI imaging devices, the apparatus comprising:
a first input port adapted for accepting a first SBI formatted digital sample data stream;
a second input port adapted for accepting a video signal from an FPA video source;
an FPA processor for rendering the video signal from the FPA video source to a second SBI formatted digital sample data stream, further comprising:
a frame grabber for acquiring an FPA video frame from the video signal; and
a frame mapper for rendering the FPA video frame into an SBI formatted digital sample data stream;
a selector for selecting an SBI formatted digital sample data stream from the first or second SBI formatted digital sample data streams for processing;
an SBI processor means for generating processed data by processing the selected SBI formatted digital sample data stream; and
an output port adapted for outputting the processed data.

20. The apparatus of claim 19 further comprising a high resolution monitor adapted to accept the processed data from the output port.

21. The apparatus of claim 20 wherein the high resolution monitor is selected from the group consisting of:
an SBI compatible monitor; and
a pixel-oriented FPA compatible monitor.

22. The apparatus of claim 20 where the high resolution monitor is a wearable heads-up display.

23. The apparatus of claim 19 further comprising an archive adapted to accept the processed data from the output port.

24. The apparatus of claim 23 wherein the archive is selected from the group consisting of:
an SBI compatible archive; and
a pixel-oriented FPA compatible archive.

25. The apparatus of claim 19 where the FPA video source is one selected from the group consisting of:
the output of an FPA camera;
the output of a video recording device;
the output of an FPA video processor; and
a computer synthesized video stream.

26. A method for allowing both an FPA video source and an SBI imaging device to use a common high resolution monitor and archive, the method comprising the steps of:
acquiring, as a first source, a series of pixel-oriented frames of video from the FPA video source;
inputting, as a second source, an SBI formatted digital sample data stream from the SBI imaging device;
rasterizing the second source into a pixel-oriented FPA format;
selecting, as an output selection, one of the first source and the second source;
rendering the output selection to a suitable high resolution FPA video signal for use with the high resolution monitor;
outputting the output selection to the high resolution monitor; and
triggering the output selection to be sent to the archive.

* * * * *